United States Patent [19]

Camaggi et al.

[11] Patent Number: 5,371,106
[45] Date of Patent: Dec. 6, 1994

[54] 3,4-DIARYL-5(H)-FURAN-2-ONE BASED COMPOUNDS WITH FUNGICIDAL ACTIVITY

[75] Inventors: Giovanni Camaggi, Novara; Lucio Filippini; Marilena Gusmeroli, both of Milan; Raul Riva, Novara; Carlo Garavaglia; Luigi Mirenna, both of Milan, all of Italy

[73] Assignee: Ministero Dell'Universita' E Della Ricerca Scientifica E Tecnologica, Rome, Italy

[21] Appl. No.: 36,500

[22] Filed: Mar. 24, 1993

[30] Foreign Application Priority Data

Mar. 26, 1992 [IT] Italy .................. MI92 A/000713

[51] Int. Cl.$^5$ .................. A61K 31/34; C07D 307/38
[52] U.S. Cl. .................. 514/473; 549/295; 549/324
[58] Field of Search .................. 549/295, 324; 514/473

[56] References Cited

U.S. PATENT DOCUMENTS

| | | | |
|---|---|---|---|
| 4,195,026 | 3/1980 | Kraus | 549/214 |
| 4,214,092 | 7/1980 | Kraus | 549/64 |
| 4,853,473 | 8/1973 | Fischer et al. | 549/326 |
| 4,968,817 | 11/1990 | Brima | 549/295 |

FOREIGN PATENT DOCUMENTS 0293748  7/1988  European Pat. Off. .

OTHER PUBLICATIONS

Chemical Abstracts, vol. 115, No. 5, Aug. 5, 1991 abstract No. 49276b, p. 804.
Indian Journal of Chemistry, Section B, vol. 29B, No. 10 Oct. 1990, pp. 954–960.

Primary Examiner—C. Warren Ivy
Assistant Examiner—A. A. Owens
Attorney, Agent, or Firm—Rogers & Wells

[57] ABSTRACT

Compounds based on 3,4-diaryl-(5H)-furan-2-one, with fungicidal activity, having the general formula (I):

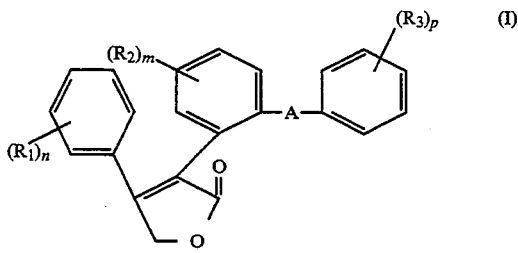

22 Claims, No Drawings

3,4-DIARYL-5(H)-FURAN-2-ONE BASED COMPOUNDS WITH FUNGICIDAL ACTIVITY

The present invention relates to compounds based on 3,4-diaryl-(5H)-furan-2-one.

More particularly, the present invention relates to compounds based on 3,4-diaryl-(5H)-furan-2-one, endowed with a high fungicidal activity, to a process for preparing them and to their use in the agrarian field, as fungicides.

Therefore, the subject-matter of the present invention are 3,4-diaryl-(5H)-furan-2-one based compounds having the general formula (I):

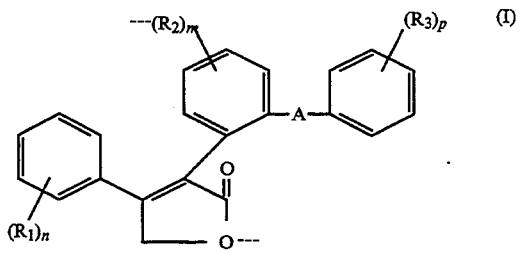

in which:
$R_1$, $R_2$ and $R_3$, which may be the same or different, represent a halogen radical, such as chloro, bromo, iodo, an either straight or branched $C_1$–$C_4$ alkyl or haloalkyl radical, a straight or branched $C_1$–$C_4$ alkoxy or haloalkoxy radical, a functional moiety, as nitrile or a $C_2$–$C_5$ carbalkoxy;

n, m and p, which may be the same or different, are integers comprised within the range of from 0 to 4;

A represents an oxygen atom, or an either straight or branched polyatomic chain having the general formula:

in which:
x and z, which may be the same or different, are 0 or 1;
y is an integer comprised within the range of from 1 to 6.

The products of general formula (I) are fungicides for agricultural applications.

Examples of $R_1$, $R_2$ and $R_3$ radicals are: methyl, ethyl, trifluoromethyl, tetrafluoroethoxy, methoxy, and so forth.

Examples of polyatomic chains A are:
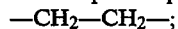
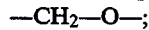
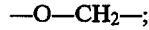
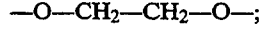
and so forth.

Compounds of general formula (I) not illustrated in the examples, but equally interesting thanks to their fungicidal activity are:

3-[2-(4-chlorobenzyloxy)phenyl]-4-(4-chlorophenyl)-(5H)-furan-2-one;

3-[2-(4-chlorobenzyloxy)phenyl]-4-(3-chlorophenyl)-(5H)-furan-2-one;

3-[2-(4-methoxybenzyloxy)phenyl]-4-(2,4-dichlorophenyl)-(5H)-furan-2-one;

3-[2-(4-chlorobenzyloxy)phenyl]-4-phenyl-(5H)-furan-2-one;

3-[2-(4-bromobenzyloxy)phenyl]-4-(4-chlorophenyl)-(5H)-furan-2-one;

3-[2-(4-trifluoromethylbenzyloxy)phenyl]-4-(4-chlorophenyl)-(5H)-furan-2-one;

3-[2-(4-(1,1,2,2-tetrafluoroethoxy)benzyloxy)phenyl]-4-(4-chlorophenyl)-(5H)-furan-2-one;

3-[2-(4-(chlorophenoxymethyl)phenyl]-4-(4-chlorophenyl)-(5H)-furan-2-one;

3-[2-(2,4-dichlorophenoxymethyl)phenyl]-4-phenyl-(5H)-furan-2-one;

3-[2-(2,4,6-trichlorophenoxymethyl)phenyl]-4-(4-chlorophenyl)-(5H)-furan-2-one;

3-[2-(2-(4-chlorophenyl)ethyl)phenyl]-4-(4-chlorophenyl)-(5H)-furan-2-one;

3-[2-(2-(2,4-dichlorophenyl)ethyl)phenyl]-4-phenyl-(5H)-furan-2-one;

3-[2-(2-(4-trifluoromethylphenyl)ethyl)phenyl]-4-(4-chlorophenyl)-(5H)-furan-2-one;

3-[2-(2-(2,4-dichlorophenoxy)ethoxy)phenyl]-4-(4-chlorophenyl)-(5H)-furan-2-one;

3-[2-(2-(4-chlorophenoxy)ethoxy)phenyl]-4-(4-chlorophenyl)-(5H)-furan-2-one;

3-[2-(3-(4-chlorophenoxy)propoxy)phenyl]-4-(4-chlorophenyl)-(5H)-furan-2-one;

3-[2-(3-(4-chlorophenoxy)-2-methylpropoxy)phenyl]-4-(4-chlorophenyl)-(5H)-furan-2-one.

The compounds according to the present invention can be obtained by means of the reaction of an arylacetic acid having the general formula (II):

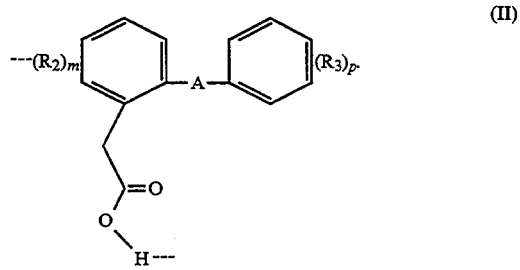

wherein $R_2$, $R_3$, m and p have the same meaning as disclosed above, with a haloketone having the general formula (III):

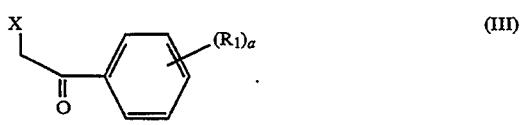

wherein X represents a halogen radical, such as chloro, bromo and iodo, $R_1$ and n have the same meaning as disclosed above.

The reaction is carried out in an aprotic polar solvent as, e.g., acetonitrile or dimethylformamide, or in a protic prolar solvent as, e.g., methyl alcohol or ethyl alcohol, and in the presence of a stoichiometric amount of an inorganic or organic base.

Examples of inorganic bases are: sodium hydrogen carbonate, potassium carbonate or potassium fluoride.

Examples of organic bases are: triethylamine or tributylamine.

The reaction is carried out at a temperature comprised within the range of from −5° C. to 80° C., and under room pressure.

In that way, the phenacyl ester is obtained which has the general formula (IV):

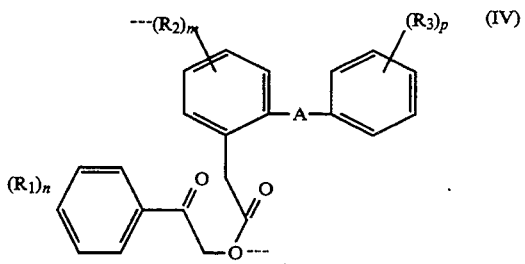

which is either directly cyclised in situ by means of the addition of another stoichiometric amount of a base, or is recovered from the reaction by means of techniques known in the prior art (extraction with solvent, organic phase drying over sodium sulfate and subsequent evaporation), is redissolved in a solvent selected from among those as disclosed hereinabove and is cyclised by means of the addition of a stoichiometric amount of a base, yielding the compound of general formula (I).

In the cyclisation reaction disclosed above, the base used preferably is an organic base, such as triethylamine or 1,4-diazo-[2:2:2]-bicyclooctane (DABCO), or an inorganic base, such as potassium carbonate. In the case where potassium carbonate is used as said base, also a phase transfer catalyst should be added, such as a crown ether, tetrabutyl ammonium chloride, or trimethyl cetyl ammonium bromide, which performs the task of activating potassium carbonate and enabling, in this way, the cyclisation reaction to take place.

The reaction temperature is comprised within the range of from room temperature to the refluxing temperature of the solvent used.

The arylacetic acid of general formula (II) is obtained according to techniques known from the prior art such as, e.g., those described in "Organic Synthesis Collection", vol. 3, page 140 (1955) and in "Journal Organic Chemistry", vol. 43, pages 2936–2938 (1978).

The haloketone of general formula (III) is a product easily available from the market.

The compounds of general formula (I) display a particularly high fungicidal activity against phytopathogenetic fungi which attach vines, cereals, Cucurbits and fruit tree cultivations.

They display both prophylactic and curative activity when applied to crops or their parts, such as, e.g., Leaves, and result to be particularly effective in order to prevent diseases caused by obliged pathogenetic fungi as, e.g., those belonging to Erysiphe and Helminthosporium genera.

The plant diseases which can be combatted with the compounds according to the present invention are, e.g., the following:

Helminthosporium on cereals;
*Plasmopara viticola* on vines;
Phytium on horticultural crops;
*Sphaerotheca fuliginea* on cucurbits (for example, cucumber);
Septoria on cereals;
*Erysiphe graminis* on cereals;
Rhynchosporium on cereals;
*Podosphaera Leucotricha* on apple trees;
Uncinula necator on vines;
*Venturia inequalis* on apple trees;
*Piricularia oryzae* on rice;
*Botrytis cinerea*;
Fusarium on cereals;
and so forth.

Besides displaying a fungicidal action of both curative and prophylactic character, as said above, the compounds of general formula (I) display a low phytotoxicity, or no phytotoxicity at all.

For the practical uses in agriculture, it is oftentimes useful to have available fungicidal compositions containing, as the active substance, one or more compounds of general formula (I).

The application of these compositions may take place on every part of the plant, e.g., on Leaves, stems, branches and roots, or to the same seeds before sowing, or the compositions may also be applied to the locus on which the plant is grown.

Compositions can be used which are in the form of dry dusts, wettable powders, emulsifiable concentrates, microemulsions, pastes, granulates, solutions, suspensions, and so forth; the selection of the composition type will depend on the specific use.

The compositions are prepared according to known methodologies, e.g., by diluting or dissolving the active substance with a solvent means and/or a solid diluent, optionally in the presence of surfactants.

As the solid diluents, or carriers, the following may be used: silica, China clay, bentonite, talc, fossil meal, dolomite, calcium carbonate, magnesia, gypsum, clays, synthetic silicates, actapulgite, sepiolite.

As liquid diluents, of course besides water, several solvent types may be used, such as, e.g., aromatic (xylenes or alkylbenzene blends), chlorinated aromatics (chlorobenzene), paraffins (petroleum fractions), alcohols (methanol, propanol, butanol, octanol), amines, amides (N,N′-dimethylformamide, N-methylpyrrolidone), ketones (acetone, cyclohexanone, acetophenone, isophorone, ethylamylketone), esters (iso-butyl acetate).

As surfactants, there may be used sodium, calcium or triethanolamine salts of alkyl sulfates, alkyl sulfonates, alkyl aryl sulfonates, polyethoxylated alkylphenols, fatty alcohols condensated with ethylene oxide, polyethoxylated fatty acids, polyethoxylated sorbitol esters, lignosulfonates.

The compositions may also contain special additives for particular purposes, such as, e.g., adhesion promoters, such as gum arabic, poly(vinyl alcohol), polyvinylpyrrolidone.

When so desired, to the compositions according to the present invention also other compatible active substances may be added, such as fungicides, phytoregulants, antibiotics, herbicides, insecticides, fertilizers.

The active substance concentration in the above said compositions may be comprised within a wide range, according to the active compound, the cultivation, the pathogenetic organism, the environmental conditions and the type of formulation adopted.

In general, the active substance concentration is comprised within the range of from 0.1 to 95%, preferably of from 0.5 to 90%.

The following examples are reported for illustrative purposes and in no way shall be construed as being limitative of the invention.

EXAMPLE 1

Preparation of
3-(2-benzyloxyphenyl)-4-(4-chlorophenyl)-(5H)-furan-2-one (Compound No. 1).

1.90 g of 2,4'-dichloroacetophenone is reacted with 2.42 g of 2-benzyloxyphenylacetic acid in 10 cc of acetonitrile, in the presence of 0.6 g of anhydrous potassium fluoride.

After being kept 1 hour at room temperature, the solution is subsequently concentrated and the resulting raw material is redissolved with ethyl acetate.

The organic solution is washed three times with water, then is thoroughly dried and is concentrated under reduced pressure.

The resulting 4-chlorophenacyl ester of 2-benzyloxyphenylacetic acid is used without any further purifications; in fact, it is dissolved in 10 cc of acetonitrile, to which 1.12 g of 1,4-diazo-[2:2:2]-bicyclooctane is added.

The resulting solution is refluxed for 8 hours.

The solvent is then evaporated, and the resulting raw product is purified by silica chromatography, with a 7:3 mixture of hexane:ethyl acetate being used as the eluent.

3.10 g of the desired product is obtained, with an overall yield of 82%.

In Table 2, the NMR spectroscopic data relevant to Compound No. 1 is reported.

EXAMPLE 2

By operating according to the modalities of Example 1, the compounds were obtained which are listed in Table 1.

The relevant NMR spectroscopic data are reported in Table 2.

EXAMPLE 3

Determination of preventive fungicidal activity against *Helinthosporium teres*.

Leaves of barley cv. Arna, grown in pots in conditioned environment are treated by being sprayed, on both leaf faces, with the compounds listed in Table 1, in solution in acetone:water at 20% by volume of acetone (the concentration of the fungicide is of 2 g/L).

After two stay days in conditioned environment at 20° C. and 70% of relative atmospheric humidity, the plants were sprayed on both their leaf faces with an aqueous suspension of conidia of *Helminthosporium teres* (250,000 conidia per cm$^3$).

After a 24-hour stay in humidity saturated environment, at 21° C., the plants were kept in a conditioned environment for fungus incubation.

At the end of said time period (12 days), all of the compounds disclosed in Table 1, at the indicated dosage, displayed a disease control of more than 90%.

EXAMPLE 4

By operating according to the same modalities as disclosed in Example 3, tests of preventive activity were carried out on the following plant/pathogen pairs:
Erysiphe cocumerinum/cucumber;
Peronospora viticola/vines;
Botrytis cinerea/tomato.

Also in these tests, all of the compounds disclosed in Table 1, at the dosage of 2 g/l, displayed a control of disease of more than 90%.

TABLE 1

| Compound No. 2 | 3-(2,4-dichlorobenzyloxyphenyl)-4-(4-chlorophenyl)-(5H)-furan-2-one |
|---|---|
| Compound No. 3 | 3-(4-bromobenzyloxyphenyl)-4-(4-chlorophenyl)-(5H)-furan-2-one |
| Compound No. 4 | 3-(2,4-difluorobenzyloxyphenyl)-4-(4-chlorophenyl)-(5H)-furan-2-one |

TABLE 2

NMR Spectroscopic data at 200 MHz (D$^6$-DMSO)

| Compound No. | |
|---|---|
| 1 | 4.85(2H)s; 5.10(2H)s; 7.20(13H)m |
| 2 | 4.90(2H)s; 5.20(2H)s; 7.15(11H)m |
| 3 | 4.90(2H)s; 5.15(2H)s; 7.20(12H)m |
| 4 | 4.88(2H)s; 5.10(2H)s; 7.18(11H)m |

We claim:

1. 3,4-diaryl-(5H)-furan-2-one based compounds having the general formula (I):

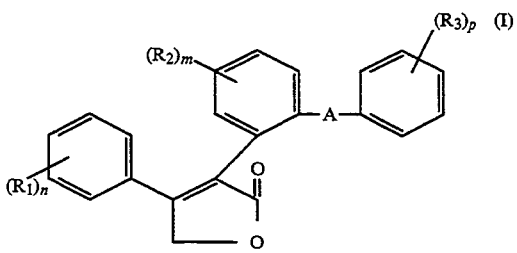

in which:

R$_1$, R$_2$ and R$_3$, which may be the same or different, represent a halogen radical, a straight or branched C$_1$–C$_4$ alkyl or haloalkyl radical, a straight or branched C$_1$–C$_4$ alkoxy or haloalkoxy radical, a nitrile or a C$_2$–C$_5$ carbalkoxy;

n, m and p, which may be the same or different, are integers within the range of from 0 to 4;

represents an oxygen atom, or a straight or branched polyatomic chain having the general formula:

$$—(O)_x—(C_yH_{2y})—(O)_z—$$

in which:

x and z, which may be the same or different, are 0 or 1;

y is an integer within the range of from 1 to 6.

2. 3,4-diaryl-(5H)-furan-2-one based compound according to claim 1, wherein the halogen radical is selected from the group consisting of chloro, bromo and iodo.

3. 3,4-diaryl-(5H)-furan-2-one based compound according to claim 1, in which R$_1$, R$_2$ and R$_3$ are selected from the group consisting of methyl, ethyl, trifluoromethyl, tetrafluoroethoxy, and methoxy.

4. 3,4-diaryl-(5H)-furan-2-one based compound according to claim 1, in which A represents a polyatomic chain selected from the group consisting of:
—CH$_2$—CH$_2$—;
—CH$_2$—O—;
—O—CH$_2$—;
—O—CH$_2$—CH$_2$—O—;
—O—CH$_2$—CH$_2$—CH$_2$—O—; and
—O—CH$_2$(CH$_3$)—CH$_2$—O.

5. 3,4-diaryl-(5H)-furan-2-one based compound according to claim 1, comprising 3-(2-benzyloxyphenyl)-4-(4-chlorophenyl)-(5H)-furan-2-one.

6. 3,4-diaryl-(5H)-furan-2-one based compound according to claim 1, comprising 3-(2,4-dichloro-benzyloxyphenyl)-4-(4-chlorophenyl)-(5H)-furan-2-one.

7. 3,4-diaryl-(5H)-furan-2-one based compound according to claim 1, comprising 3-(4-bromo-benzyloxyphenyl)-4-(4-chlorophenyl)-(5H)-furan-2-one.

8. 3,4-diaryl-(5H)-furan-2-one based compound according to claim 1, comprising 3-(2,4-difluoro-benzyloxyphenyl)-4-(4-chlorophenyl)-(5H)-furan-2-one.

9. Antifungal composition for agricultural purposes, comprising compounds based on 3,4-diaryl-(5H)-furan-2-one having the general formula (I):

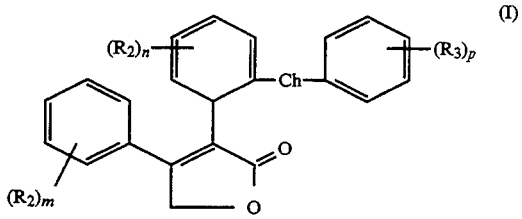

(I)

in which:
$R_1$, $R_2$ and $R_3$, which may be the same or different, represent a halogen radical, a straight or branched $C_1$-$C_4$ alkyl or haloalkyl radical, a straight or branched $C_1$-$C_4$ alkoxy or haloalkoxy radical, a nitrile or a $C_2$-$C_5$ carbalkoxy;

n, m and p, which may be the same or different, are integers within the range of from 0 to 4;

Ch represents an oxygen atom, or an either straight or branched polyatomic chain having the general formula:

in which:
x and z, which may be the same or different, are 0 or 1;
y is an integer within the range of from 1 to 6.

10. Antifungal composition for agricultural purposes according to claim 9, in which $R_1$, $R_2$ and $R_3$ are selected from the group consisting of methyl, ethyl, trifluoromethyl, tetrafluoroethoxy, and methoxy.

11. Antifungal composition for agricultural purposes according to claim 9, in which A represents a polyatomic chain selected from the group consisting of:
—$CH_2$—$CH_2$—;
—$CH_2$—O—;
—O—$CH_2$—;
—O—$CH_2$—$CH_2$—O—;
—O—$CH_2$—$CH_2$—$CH_2$—O—; and
—O—$CH(CH_3)$—$CH_2$—O—.

12. Antifungal composition for agricultural purposes according to claim 9, comprising 3-(2-benzyloxyphenyl)-4-(4-chlorophenyl)-(5H)-furan-2-one.

13. Antifungal composition for agricultural purposes according to claim 9, comprising 3-(2,4-dichlorobenzyloxyphenyl)-4-(4-chlorophenyl)-(5H)-furan-2-one.

14. Antifungal composition for agricultural purposes according to claim 9, comprising 3-(4-bromobenzyloxyphenyl)-4-(4-chlorophenyl)-(5H)-furan-2-one.

15. Antifungal composition for agricultural purposes according to claim 9, comprising 3-(2,4-difluorobenzyloxyphenyl)-4-(4-chlorophenyl)-(5H)-furan-2-one.

16. Process for preparing the compounds according to claim 1 which consists of the reaction of an arylacetic acid having the general formula (II):

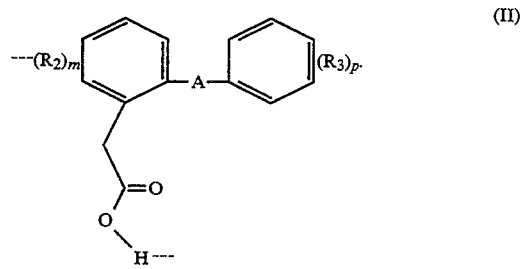

(II)

wherein $R_2$, $R_3$, m and p have the same meaning as claim 1,
with a haloketone having the general formula (III):

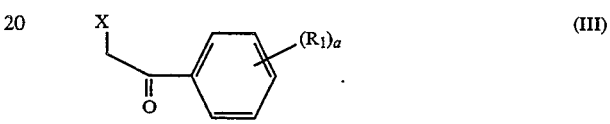

(III)

wherein X represents a halogen radical, $R_1$ and n have the same meaning as in claim 1, in an aprotic polar solvent or in a protic polar solvent and in the presence of a stoichiometric amount of an inorganic or organic base, at a temperature within the range of from $-5°$ C. to $80°$ C., with the phenacyl ester being thus obtained which has the general formula (IV):

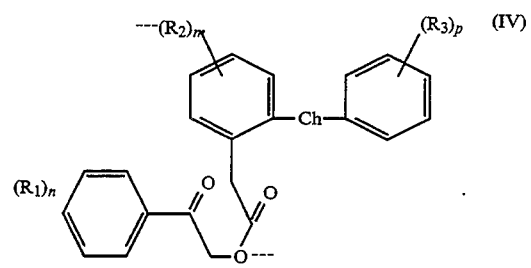

(IV)

which is cyclised in situ by means of the addition of a stoichiometric amount of a base, yielding the compound of general formula (I).

17. A process according to claim 16, wherein the compound obtained which has the general formula (IV) is cyclised by recovering the compound from the reaction, redissolving the compound in a solvent selected from the group consisting of an aprotic polar solvent or a protic polar solvent, and cyclising by the addition of a stoichiometric amount of a base.

18. Process according to claim 16, in which the cyclisation reaction is carried out in the presence of an organic base, or of an inorganic base.

19. A process according to claim 18, wherein the organic base is selected from the group consisting of triethylamine and 1,4-diazo-[2:2:2]-bicycloctane.

20. A process according to claim 18, wherein the organic base is comprised of potassium carbonate.

21. Process according to claim 20, in which, the cyclisation reaction takes place in the presence of a phase transfer catalyst.

22. Method for combatting fungal infections, consisting in applying onto the plants, leaves, stems, branches and roots, or to the seeds before sowing, or to the locus on which the plant grows, antifungal compositions according to claim 9.

* * * * *

UNITED STATES PATENT AND TRADEMARK OFFICE
CERTIFICATE OF CORRECTION

PATENT NO. : 5,371,106
DATED : December 6, 1994
INVENTOR(S) : Giovanni Camaggi et al.

It is certified that error appears in the above-identified patent and that said Letters Patent is hereby corrected as shown below:

In Column 6: in Claim 1, in line 42, before the word "represents" --A-- should be added.

In Column 7: in Claim 9, in the formula, "$(R_2)_n$" should read as --$(R_2)_m$--; "$(R_2)_m$" should read as --$(R_2)_n$--; and "Ch" should read as --A--.

In Column 7: in Claim 9, in line 34, "Ch" should read as --A--.

In Column 8: in Claim 16, in Formula III, "$(R_1)_a$" should read as --$(R_1)_n$--.

In Column 8: in Claim 16, in Formula IV, "Ch" should read as --A--, and $(R_1)_n$ should be connected to the benzene ring with a line.

Signed and Sealed this

Seventeenth Day of October, 1995

Attest:

BRUCE LEHMAN

*Attesting Officer*     *Commissioner of Patents and Trademarks*